United States Patent [19]

Handrick et al.

[11] 4,185,023
[45] Jan. 22, 1980

[54] CATALYTIC OXIDATIVE PROCESS FOR THE MANUFACTURE OF ANTHRAQUINONE FROM O-BENZYL TOLUENE

[75] Inventors: Kurt Handrick, Essen-Steele; Georg Kölling, Essen-Bredeney; Clemens Linden, Essen-Bergerhausen; Günter Droll, Jr., Moers, all of Fed. Rep. of Germany

[73] Assignee: Bergwerksverband GmbH, Essen, Fed. Rep. of Germany

[21] Appl. No.: 8,387

[22] Filed: Feb. 1, 1979

[30] Foreign Application Priority Data

Feb. 2, 1978 [DE] Fed. Rep. of Germany ....... 2804417

[51] Int. Cl.² .......................... C07C 49/68; C09B 1/00
[52] U.S. Cl. ..................................................... 260/369
[58] Field of Search ........................................ 260/369

[56] References Cited

U.S. PATENT DOCUMENTS 4,036,861  7/1977  Togo et al. ........................... 260/369

OTHER PUBLICATIONS

Chemical Abstract, vol. 82, No. 43096w, 1975, Tsutoma et al., "o-Benzoylbenzoic Acid and Anthraguinone".

Primary Examiner—Patrick Garvin
Assistant Examiner—Raymond K. Covington
Attorney, Agent, or Firm—Michael J. Striker

[57] ABSTRACT

A process for the manufacture of anthraquinone, in which o-benzyl-toluene is oxidized with air or an oxygen-containing gas in an acetic acid solution in the presence of cobalt, manganese and bromine salts as catalysts, to which solution sufficient acetic anhydride is added to bind the reaction water, thereby keeping the acid concentration constant. The crude o-benzoyl-benzoic acid is then esterified with methanol, the methyl ester distilled from the reaction mixture and heated with concentrated sulfuric acid to yield anthraquinone in good yield and of a high degree of purity.

6 Claims, No Drawings

CATALYTIC OXIDATIVE PROCESS FOR THE MANUFACTURE OF ANTHRAQUINONE FROM O-BENZYL TOLUENE

BACKGROUND OF THE INVENTION

The invention concerns a process for the manufacture of anthraquinone through the oxidation of o-benzyl-toluene with air or oxygen-containing gases in an acetic acid solution in the presence of cobalt, manganese and bromide salts at temperatures of about 100°–150° C. and atmospheric or elevated pressures.

Anthraquinone is a starting material in the manufacture of valuable dyes which are required by the textile industry in ever-increasing amounts.

From DT-OS 20 50 799, it is known to oxidize o-benzyl-toluene with air in acetic acid solution with the addition of catalytic amounts of cobalt bromide and manganese acetate at a temperature of 160° C. and a pressure of 20 bar. The weight ratio of o-benzyl-toluene to acetic acid approaches about 1:12. The o-benzoyl-benzoic acid is not isolated, but instead is directly converted to a raw anthraquinone under heating with concentrated sulfuric acid; purification is effected by extraction with benzene. An unpurified anthraquinone crystallizes out with a melting range of 279°–282° C. in a yield of 72% of theory, calculated from the starting o-benzyl-toluene.

It is further known from the Japanese patent publication 49-75563 (Ref: Chem. Abstr. 1975, 43096w) to oxidize o-benzyl-toluene in an aliphatic carboxylic acid, for example acetic acid, in the presence of cobalt salts and bromine compounds, to which manganese salts may also be added as additional catalytic agents. The reaction, carried out at the atmospheric pressure or slightly elevated pressure at temperatures from 70° to 200° C. with air or oxygen-containing gases, yields o-benzoyl-benzoic acid with an anthraquinone content of between 3 and 9% as product. The oxidation in the acetic acid solution is carried out in general with a weight ratio of o-benzyl-toluene to acetic acid of about 1:10. After a reaction time of 4–5.5 hours o-benzoyl-benzoic acid in a yield of about 90–92.5% of theory is recovered, along with about 3–4% of theory of anthraquinone. The purity of the o-benzoyl-benzoic acid is not further discussed. The product is then heated with a minimal amount of concentrated sulfuric acid to about 250°–350° C.; in order to purify the thus-obtained anthraquinone, it is distilled at normal pressure. The degree of purity of this product is also not given. It is further noted that it is advantageous to add to the reaction mixture a solvent which does not mix with water such as benzene, chlorobenzene or dichlorobenzene in order to eliminate the water produced by the reaction as an azeotrope. For example, half of the acetic acid can be replaced according to the publication by chlorobenzene; however, an azeotropic distillation during the oxidation is not achieved by following the example of the Japanese publication.

DESCRIPTION OF THE INVENTION

It is therefore a goal of the invention to improve the known methods and to obtain high yields of pure anthraquinone through the catalytic oxidation of o-benzyl-toluene with oxygen and the cyclization of the product o-benzoyl-benzoic acid with concentrated sulfuric acid.

This is achieved through the inventive process by first carrying out the oxidation in an acetic acid solution with the addition of acetic anhydride to bind the reaction water produced. The crude o-benzoyl-benzoic acid is then esterified in a conventional manner known per se, the methyl ester distilled and when necessary recrystallized, and the purified ester converted to anthraquinone by heating with concentrated sulfuric acid at a temperature of about 150° C.

If the amount of acetic anhydride is sufficient to take up all the reaction water, the acetic acid concentration does not fall below 98 weight-% during the reaction, and generally does not fall below 100 weight-%. From this it follows, that the oxidation can be carried out without reduction in the yield with a weight ratio of o-benzoyl-toluene to solvent, consisting of acetic acid and acetic anhydride, of between 1:3 to 1:4. Without the addition of acetic anhydride a ratio of at least 1:10 is required, in order to keep the concentration of the previously 100% acetic acid from falling below the noted value of 98 weight-%. In addition to the decrease in reaction volume, the addition of acetic anhydride has further advantages: the oxidation occurs more quickly, reducing the reaction time; the production of anthraquinone is marginally increased; above all, the purity of the o-benzoyl-benzoic acid is increased, with the corresponding increase in the yield of pure anthraquinone.

It has further been determined that in order to achieve a high yield the amounts of catalysts added are important. The total amount of Cobalt$^{II}$-ions (for example, in the form of cobalt (II) acetate.4H$_2$O) and manganese$^{II}$-ions (e.g., in form of manganese (II) acetate.4H$_2$O) should lie between 1.2–1.8% of the amount of o-benzyl-toluene; a weight ratio of Co$^{++}$:Mn$^{++}$ from between 1:1 to 5:1 is advantageous. Without the addition of manganese salts the yield of o-benzoyl-benzoic acid is markedly reduced. The amount of bromide ion is less critical; an amount of about 0.2–0.5% of the total o-benzyl-toluene content is sufficient.

The oxidation of the o-benzyl-toluene with air or oxygen can be carried out at 105°–110° C. at atmospheric pressure or preferably at higher temperatures under pressure; in the latter instance, temperatures of 120°–130° C. and pressures from 10–20 bar are sufficient. After the reaction the anthraquinone produced can be filtered off and the solvent distilled. The o-benzoyl-benzoic acid is advantageously extracted with alkali, through which process the metal catalysts can be recovered in the form of oxides. After acidification of the extract the crude acid precipitates. It is recovered in good yield and exhibits an acid number of 240–244 (Theory: 248), corresponding to a purity of about 97%. The major impurities present are colored substances.

In spite of its already high degree of purity, the direct mixing of the crude o-benzoyl-benzoic acid with hot concentrated sulfuric acid gives a strongly colored anthraquinone contaminated with decomposition products. The crude acid is therefore esterified with methanol, and the methyl ester separated from the by-products through a distillation. The esterification may be effected in the conventional manner in the presence of acid catalysts such as hydrochloric, sulfuric or p-toluenesulfonic acids, or alternatively without catalysts under pressure at temperatures above 200° C. The pure o-benzoyl-benzoic acid methyl ester distills off in the range 177°–181° C. under a pressure of 8 Torr. It solidifies to colorless crystals with a melting point of 52.5° C.

It is possible that even after distillation the ester is still slightly colored. In this case it can be recrystallized; the solvent of choice is isopropyl alcohol. The ester precipitates in granular crystalline form and in high yield. The fraction remaining in the mother liquor can be redistilled after removal of the isopropyl alcohol and the distillate again recrystallized.

The o-benzoyl-benzoic acid methyl ester is then mixed with the known materials for effecting the cyclization of o-benzoyl-benzoic acid without any saponification of the ester. It is surprizing that the methyl ester may be converted quantitatively to anthraquinone upon heating to about 150° C. with concentrated sulfuric acid, the technically preferred method for cyclization of o-benzoyl-benzoic acid. It is known that strong mineral acids can saponify esters; however, such reactions are generally not uniform and complete.

The invention may be better understood through the following examples.

EXAMPLE 1

A 1 m long pressure reactor provided with a heating jacket and having a reaction volume of about 1.2 l, is charged with a solution of 121.4 g o-benzyl-toluene (⅔ Mol), 360 ml of dry acetic acid, 110 ml acetic anhydride, 6.0 g cobalt (II) acetate.4H$_2$O, 1.5 g manganese (II) acetate.4H$_2$O and 0.5 g ammonium bromide. The system also includes a pressure cooler of approximately the same length, provided with an expansion vent and a manometer. The reactor is heated up to about 125° C.; about 10 liters/minute of air is introduced through the base of the reactor via an inlet duct provided with a frit. The pressure is held constant at about 20 bar. After about 2 hours the oxygen uptake ceases. After release of the pressure the contents of the reactor is poured out while still hot. After cooling the anthraquinone which falls out in the form of yellow needles is filtered off (dry weight 9.5 g=7% of theory; melting point 286° C). The filtrate is heated to evaporate off the acetic acid; the residue is extracted with dilute sodium hydroxide. After acidification of the alkaline extract the crude o-benzoyl-benzoic acids precipitates out (133 g=88.3% of theory; acid number 242; color=light brown).

The crude acid is subsequently esterified with methanol in the presence of a catalytic amount of concentrated sulfuric acid. After the usual work up 6.4 g of nonesterified acid is recovered, which may be added to the next batch; 133.5 g of the raw eater is also obtained. The ester is then distilled over a short column over the range 178°–180° C. at 8 Torr; it solidifies to colorless crystals with a melting point of 52.5° C. The yield at this stage is 129.5 g. In order to effect the cyclization the o-benzoyl-benzoic acid methyl ester is heated to 150° C. with 400 ml concentrated sulfuric acid for 1 hour. The solution is stirred in water after cooling. 110 g of pure anthraquinone with a melting point of 286° C. thereby precipitates.

If the yield from the o-benzoyl-benzoic acid which was separated from the methyl ester after the esterification step is added into the calculation, the total yield of anthraquinone, based on the starting o-benzyl-toluene, approaches 91% of theory.

Comparison Example 2a

The oxidation is carried out according to Example 1 without the addition of acetic anhydride; in its place a further 110 ml of dry acetic acid is added.

After an oxidation period of about 3 hours no more oxygen is taken up. The work-up of the reaction mixture yields 3.8 g anthraquinone and 78.7 g (52% of theory) o-benzoyl-benzoic acid with an acid number of 224. The remainder of the oxidation product consists primarily of o-benzoyl-toluene.

Comparison Example 2b

The reactor described in Example 1 is charged with a mixture of 60.7 g o-benzyl-toluene (⅓ Mol), 607 ml dry acetic acid, 3 g cobalt (II) acetate.4H$_2$O, 0.5 g manganese (II) acetate.4H$_2$O and 3.0 g cobalt (II) bromide.6-H$_2$O. The reaction is carried out as described above. The uptake of oxygen is completed after about 3 hours. After the analogous work up 2.2 g anthraquinone (3.2% of theory) and 68.1 g crude o-benzoyl-benzoic acid (90.4% of theory) are recovered; the acid number approaches 226, and the color is medium brown. Heating of a small sample with concentrated sulfuric acid yields a darkly-colored anthraquinone.

Esterification of the raw o-benzoyl-benzoic acid with methanol gives in addition to 3.5 g of unesterified acid a distillate of 63.0 g of colorless methyl ester, that after treatment with concentrated sulfuric acid at 150° C. yields 54.4 g pure anthraquinone with a melting point of 286° C.

The total yield of anthraquinone after calculation of the amount derived from the o-benzoyl-benzoic acid which was not esterified approaches 86% of theory.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed as new and desired to be protected by Letters Patent is set forth in the appended claims:

1. A process for the manufacture of anthraquinone, comprising oxidizing o-benzyl-toluene with air or an oxygen-containing gas in an acetic acid solution containing cobalt, manganese and bromine salts to which sufficient acetic anhydride is added to bind all water produced during said oxidation, at a temperature between about 100° and 150° C. and at atmospheric or elevated pressure, to produce crude o-benzoyl-benzoic acid; esterifying said crude o-benzoyl-benzoic acid to produce a corresponding methyl ester; distilling said methyl ester from the reaction mixture; and heating said methyl ester with concentrated sulfuric acid at a temperature of about 150° C. to yield anthraquinone.

2. A process as defined in claim 1, further comprising a recrystallization of said methyl ester from isopropyl alcohol.

3. A process as defined in claim 1, wherein the weight ratio of o-benzyl-toluene to solvent, comprised of acetic acid and acetic anhydride, is between about 1:3 to 1:4.

4. A process as defined in claim 1, wherein the total amount of cobalt$^{II}$ and manganese$^{II}$ ions is approximately 1.2 to 1.8% of the amount of o-benzyl-toluene.

5. A process as defined in claim 4, wherein the ratio of cobalt$^{II}$ to manganese$^{II}$ ions is about 1:1 to 5:1 by weight.

6. A process as defined in claim 1, wherein the amount of bromide ions is approximately 0.2 to 0.5% of the amount of o-benzyl-toluene.

* * * * *